United States Patent

Gumbs

[11] Patent Number: 5,173,811
[45] Date of Patent: Dec. 22, 1992

[54] NONLINEAR OPTICAL SHIELD

[75] Inventor: Ronald W. Gumbs, East Brunswick, N.J.

[73] Assignee: Gumbs Associates, Inc., East Brunswick, N.J.

[21] Appl. No.: 775,272

[22] Filed: Oct. 11, 1991

[51] Int. Cl.$^5$ .................... G02B 5/23; F21V 9/00; H01S 3/10
[52] U.S. Cl. .................... 359/885; 359/890; 351/213
[58] Field of Search .............. 359/227, 358, 885, 886, 359/890; 385/122; 356/432, 441; 351/213

[56] References Cited

U.S. PATENT DOCUMENTS

| | | | |
|---|---|---|---|
| 4,474,857 | 10/1984 | Vaughn | 427/164 |
| 4,548,473 | 10/1985 | Lo et al. | 359/885 |
| 4,601,532 | 7/1986 | Musser et al. | 359/885 |
| 4,803,688 | 2/1989 | Lawaroly | 372/21 |
| 4,933,110 | 6/1990 | Tucker | 359/885 |
| 4,937,017 | 6/1990 | LaForce et al. | 359/890 |

FOREIGN PATENT DOCUMENTS

| | | |
|---|---|---|
| 2017044 | 7/1985 | Japan . |
| 2124502 | 11/1985 | Japan . |
| 1208213 | 3/0000 | United Kingdom . |

OTHER PUBLICATIONS

Thomas, I. M.; SPIE O-E Lase '88, L.A. Calif., Jan. 10, 1988, NTIS DE 88006230/XAB; abst. only supplied.

*Primary Examiner*—Nelson Moskowitz
*Attorney, Agent, or Firm*—Arthur L. Lessler

[57] ABSTRACT

An optical shield which is transparent to ambient light but which blocks high intensity light such as that from a laser, with a response speed on the order of several picoseconds or less, to provide eye protection and to protect light sensors from laser beams. The shield is a multilayer structure with layers in which colloidal silica particles are dispersed in a transparent polymer binder having an index of refraction close to that of the silica particles under ambient light conditions. The application of multiple sealant layers of pure binder material results in improved transmittance of ambient light. High intensity light such as that from a laser causes third order nonlinear optical effects, particularly photorefractive effects, in the silica which change its effective index of refraction so that the mismatch between the effective index of refraction of the silica and the index of refraction of the binder causes scattering of the incident light. The shield is effective over a broad radiation band including near infrared and ultraviolet portions of the spectrum as well as the entire visible light range.

25 Claims, 4 Drawing Sheets

| | POLYMER/SILICA RATIO IN TOLUENE | NUMBER OF COATS | OVERALL PERCENT TRANSMITTANCE | OVERALL ΔOD | |
|---|---|---|---|---|---|
| 39 — ADDITIONAL ACTIVE LAYERS | POLYETHYLMETHACRYLATE | 16 | 79 | 1.2 | ADDITIONAL SEALANT LAYERS |
| 35 — SEALANT LAYERS | 10/6 | 4 | 18 | 1.1 | 37 |
| 31 | POLYVINYL ALCOHOL | 1 | 81 | 0.9 | BARRIER LAYER |
| 30 | POLYETHYLMETHACRYLATE | 16 | 85 | 0.9 | 33 — ACTIVE LAYERS |
| 32 | 10/6 | 4 | 24 | 1.0 | SUBSTRATE |
| 36 — SEALANT LAYERS | | GLASS | 92 | 0.0 | ACTIVE LAYERS |
| | 10/6 | 4 | 24 | 1.0 | 34 |
| | POLYETHYLMETHACRYLATE | 16 | 85 | 0.9 | BARRIER LAYER |
| | POLYVINYL ALCOHOL | 1 | 81 | 0.9 | 38 |
| ADDITIONAL ACTIVE LAYERS | 10/6 | 4 | 18 | 1.1 | ADDITIONAL SEALANT LAYERS |
| 40 | POLYETHYLMETHACRYLATE | 16 | 79 | 1.2 | |

FIG. 4

NONLINEAR OPTICAL SHIELD

BACKGROUND OF THE INVENTION

This invention relates to a nonlinear optical shield which is particularly suitable for eye protection and protection of photosensors from high intensity light such as that from a laser beam.

The use of lasers has become widespread, especially in military equipment on the battlefield—to the point where there is a need for broadband passive nonlinear shields which permit normal or ambient intensity levels of visible light to pass through them, and which are capable of virtually instantaneously (within several picoseconds or less) blocking high intensity pulsed or continuous wave laser beams in the visible, near infrared and ultraviolet portions of the spectrum, to prevent eye damage and damage to photosensors in the path of the laser beam.

The sensitivity of the human eye to injury from laser beams

The sensitivity of the human eye to brightness can vary by a factor of 100 billion. The dark adapted eye is capable of detecting single photons and it works with nearly 100% quantum efficiency. These extraordinary qualities make the eye extremely vulnerable to laser damage.

Even though vision is limited to the eye's response over a relatively narrow wavelength visible region (0.4 to 0.7 microns), light from outside this region has a profound effect on sight. The cornea absorbs infrared radiation (1.4–10 microns) and the cornea combined with the lens absorbs near ultraviolet radiation (0.2–0.4 microns).

Ultraviolet and infrared radiation can damage the cornea by causing photokeratitis, corneal burns and cataracts and thereby impair vision. The greatest danger, however, comes from visible to near-infrared radiation (0.4–1.4 microns). which the cornea and the lens transmit, focusing onto the retina with optical gains (increases in intensity) on the order of $10^5$. There is, therefore, a critical need to protect human eyes from hazardous radiation in the 0.4 to 1.4 micron or 400 to 1400 nanometer wavelength range.

Currently available laser protective devices which utilize light absorbing or reflecting materials can provide protection only at fixed, predetermined wavelengths. With the advent of tunable lasers, the need for ocular and sensor protection against multiwavelength and frequency agile lasers has become evident.

With such protection devices it is essential that transmittance in the visible region be sufficient to maintain vision under all indoor and outdoor conditions of illumination, from moonless nights to bright sunny days.

The prior art

In order to meet the aforementioned requirements, structures are needed which have transmittances of 20% or more under ambient conditions and which experience optical density decreases of at least four[1], i.e. which attenuate the light intensity by a factor of 10,000 or more. Because of the high rate of rise of the leading edges of laser beam pulses, such structures must have very fast response times in order to prevent a damage-inducing amount of beam energy from traversing the structure. At the same time, such structures must have recovery times of 0.1 second or less, so that normal vision is restored as soon as the flash of the laser beam is past, thus minimizing the risk of accident due to interruption of vision for a significant period of time.

[1] The change in optical density $\Delta OD$ introduced by an optical element may be defined as $\log \Delta I_i/\Delta I_o$, where $\Delta I_i$ is the change in incident light intensity and $\Delta I_o$ is the corresponding change in output light intensity.

In an effort to meet the aforementioned objectives, devices have been proposed utilizing various nonlinear optical effects, to block laser beams by absorption, dispersion or scattering. Recent efforts have focused on the possible exploitation of organic materials exhibiting relatively fast response third order nonlinear optical effects such as photo-refraction,[2] Kerr effect, and some other effects.[3] Materials which exhibit third order nonlinear optical effects are commonly referred to as $\chi^{(3)}$ materials, the term $\chi^{(3)}$ referring to the third order susceptibility parameter.

[2] In a photorefractive material the effective index of refraction varies with the intensity of light in the material.
[3] Eye/Sensor Protection Against Laser Irradiation; Organic Nonlinear Optical Materials, Michael E. Boyle and Robert F. Cozzens, Polymeric Materials Branch, Chemistry Division, Naval Research Laboratory Memorandum Report 6482, Jun. 12, 1989.

One such proposal is for a device using a dispersion of $\chi^{(3)}$ microparticles in a polymeric host.[4] In this proposed device the index of refraction of the particles would be similar to that of the host to make the device transparent under ambient conditions; and at high optical intensities photorefractive effects in the microparticles would cause an index of refraction mismatch resulting in scattering of incident light. However, efforts to make such a proposed device utilizing known $\chi^{(3)}$ materials were not successful.[5]

[4] Eye/Sensor Protection Against Laser Irradiation; Organic Nonlinear Optical Materials, Michael E. Boyle and Robert F. Cozzens, Polymeric Materials Branch, Chemistry Division, Naval Research Laboratory Memorandum Report 6482, Jun. 12, 1989, p. 46 and FIG. 29.
[5] Cf. Nonlinear Optical Materials, David F. Eaton, Science magazine, American Association For The Advancement of Science, Vol. 253, pp. 281-287, Jul. 19, 1991; Chemists Crucial To Progress in Nonlinear Optical Materials, Chemical & Engineering News, Science/Technology, pp. 21-25, Jun. 11, 1990; Optical Material Shows High Tertiary Nonlinear Effects, Laser Focus World, Optics Industry Report, p. 64, Jul. 1990.

Devices have been developed which incorporate diffraction holograms and act as filters to cause interference effects which scatter incident light at specific wavelengths.[6] Such devices, however, can provide protection only at fixed, predetermined wavelengths; and therefore cannot be effective against multiwavelength or frequency agile lasers. Further, as the number or width of the fixed attenuation bands in the visible light range required to block the various lasers that may be encountered increases, both the photopic and scotopic eye transmissions rapidly decrease with the use of such permanent and static filters. Further, interference filters are ineffective at large angles of incidence and are useless when several filters are stacked.

[6] From Armaments to Eyes At Army Materials Lab, Lasers & Optronics, p. 25, November 1990.

Devices have also been developed which incorporate multiple layer dielectric filters to provide a narrow passband in the visible range which does not correspond to the wavelength of any known laser.[7] Such devices, however, have poor transmittance because they transmit only a small portion of the visible spectrum, and leave open a band in which harmonics or other spectral elements of laser beams may intrude.

[7] U.S. Pat. No. 3,519,339 to T. J. Hutchinson et al.; U.S. Pat. No. 3,791,721 to Helfrich.

Accordingly, an object of the present invention is to provide a dynamic, reversible and broad band shield that can optically and passively switch in several picoseconds or less from a transparent state to a scattering or reflecting state with a sufficient change in optical density to effectively block laser light at intensities exceeding 1.0 µJ/cm$^2$, with a recovery time of less than 0.1 second.

SUMMARY OF THE INVENTION

As herein described, according to one aspect of the invention there is provided a nonlinear optical shield including an active layer comprising colloidal silica particles dispersed in a transparent binder, said particles and binder having indices of refraction on the same order.

According to a further aspect of the invention there is provided a nonlinear optical shield including a transparent substrate having opposed major surfaces. An active layer is disposed on one of the major surfaces. The active layer comprises colloidal silica particles dispersed in a transparent binder. A transparent sealant layer is disposed on a surface of the active layer remote from the substrate.

According to a further aspect of the invention there is provided a process for manufacturing a nonlinear optical shield, wherein an active layer comprising colloidal silica particles dispersed in a transparent binder is deposited on a major surface of a transparent substrate, and the active layer is treated to increase its transmittance by reducing agglomeration of the silica particles therein. The treatment may involve partially dissolving or liquefying the active layer.

IN THE DRAWING

FIG. 4 shows in diagrammatic fashion the structure of an optical shield according to a preferred embodiment of the present invention.

ADVANTAGES OF THE INVENTION OVER THE PRIOR ART

Figure 1:
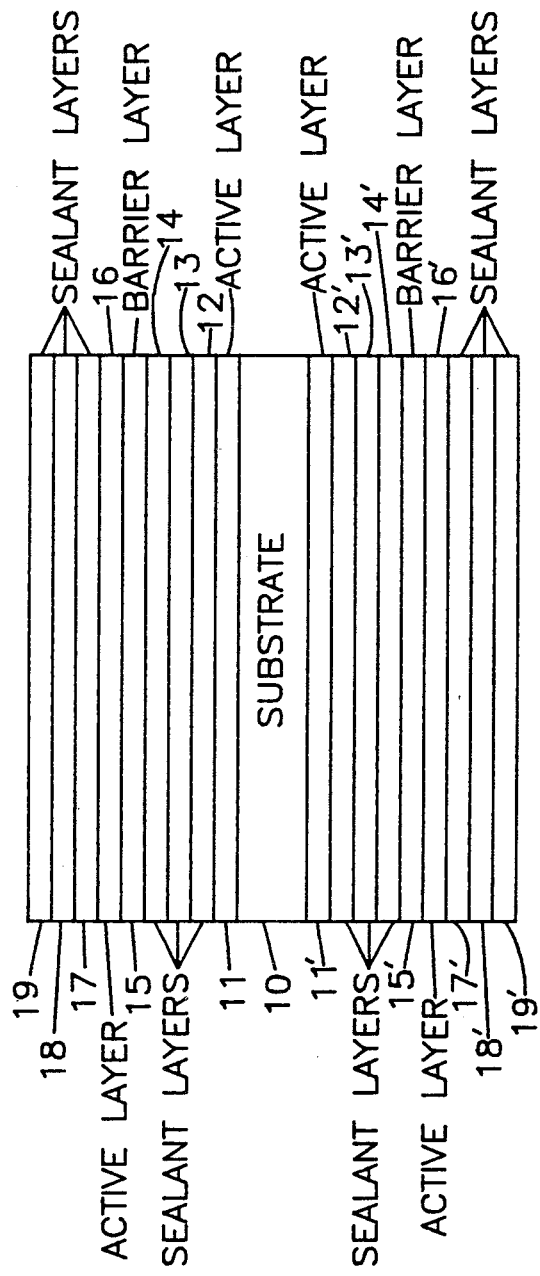
FIG. 1 shows a multilayer nonlinear optical shield according to an illustrative embodiment of the present invention.

The present invention provides a passive device which effectively blocks laser light over the entire visible spectrum as well as the near infrared and near ultraviolet ranges, with a response time of several picoseconds or less, a recovery time of less than 0.1 second, and a transmittance of 20% or more in the visible light range—a level of performance well beyond that of prior art devices, and which provides a far greater margin of safety that has hitherto been available.

GENERAL DESCRIPTION

While bulk silica does not exhibit significant third order nonlinear optical properties, it has been discovered that particles of colloidal silica[8] behave to a considerable extent as though they have $\chi^{(3)}$ material properties, when they are dispersed in a transparent organic binder such as polyethylmethacrylate to form an active layer on a transparent substrate such as glass.
[8] Colloidal particles are generally considered to be those having sizes in the range of 1 to 500 nanometers.

Colloidal silica has an index of refraction of 1.46 and polyethlymethacrylate has an index of refraction of 1.485, so that there is little scattering due to refractive index mismatch between the particles and the binder under ambient light conditions. When exposed to a laser beam with an intensity of 1 µJ/cm$^2$ (one microjoule per square centimeter) or more, a shield incorporating multiple active layers of the aforementioned type has demonstrated a change in optical density of 4 or more[9] at a speed of several picoseconds or less; while having a transmittance of 20% or more for visible light and a recovery time of less than 0.1 second after termination of exposure to the laser beam.
[9] Permitting no more than 1/10,000 of the increase in incident light intensity to pass through the shield.

When only a single active layer is deposited on the substrate, the transmittance of the device is relatively low, typically on the order of 10%, even though the silica typically comprises no more than 6% of the active layer by weight. It is believed that this poor transmittance is due to agglomeration of the colloidal silica particles.

However, the transmittance is remarkably increased when the active layer is coated with successive sealant layers by immersion in a liquid comprising the binder material. It is believed that these immersion steps partially dissolve or liquefy the active layer, breaking up agglomeration clusters and causing diffusion, leaching or migration of some silica particles into the sealant layers. Thus the original heavy concentration of colloidal silica particles in the active layer is believed to be partially distributed to the sealant layers, resulting in greatly improved uniformity of distribution of the silica particles and thus substantially enhancing the transmittance of the shield.

Instead of using liquid binder material to form each sealant layer, another transparent substance may be used in which the binder in the active layer is soluble.

When a sufficient number of sealant layers has been applied to provide a high level of transmittance through the substrate, active layer and sealant layers, a transparent barrier layer is deposited on the exposed surface of the top sealant layer, by immersing said exposed surface in a liquid which does not act as a solvent for the underlying sealant layer. An additional active layer is then deposited atop the barrier layer, and the process is repeated until the desired combination of optical density change and transmittance characteristics is obtained.

Each active layer preferably has a thickness in the range of 10 to 50 microns, and when initially deposited contains 5% to 40% silica by weight.

Each barrier layer may comprise a material which has an index of refraction sufficiently different from the index of refraction of the adjacent additional active layer so that significant refraction of incident light occurs at the interface between the barrier layer and the adjacent additional active layer.[10] In a typical shield having multiple active layers, the refraction effects at interfaces between barrier layers and active layers cause an incident laser beam to travel a zigzag path which results in an increased path length in the active layers, enhancing the scattering effect and increasing the effective optical density of the shield.
[10] In the preferred embodiment the barrier material is polyvinyl alcohol which has an index of refraction of 1.49, very close to the 1.485 index of refraction of the polyethylmethacrylate binder in the active layer. While tests were not conducted with a barrier material of materially different index of refraction, such a material should provide enhanced performance due to the resulting increase in optical path length (see Equation 1).

Other binders (organic polymers in general and acrylic plastics in particular being preferred) may be used which have indices of refraction on the same order as silica, with binders having indices of refraction in the range of 1.4 to 1.5 being preferred. The binder should preferably be one which is not significantly photorefractive. Alternatively, binders may be used which exhibit changes of refractive index with increasing light intensity which are opposite in direction to those of the silica particles in the active layer.

Suitable binders include polyethyl methacrylate, polyethyl acrylate, polybutyl acrylate, poly 2-ethylhexyl acrylate, polymethyl methacrylate, polyethylmethacrylate, polybutylmethacrylate, various copolymers and mixtures of polymers of acrylates and methacrylates, polyvinyl acetate with different percentages of hydrolysis including polyvinyl alcohol, polystyrene, poly p-methyl styrene, poly α-methyl styrene, copolymers of vinyl chloride, copolymers of vinylidene chloride, copolymers of ethylene such as with vinyl acetate and vinyl chloride, cellulose acetate, cellulose triacetate, cellulose nitrate, cellulose acetate isobutyrate, silicone resins, polyvinylcarbazole, polyvinylbutyral and polyvinylformal.

Suitable substrates include inorganic oxide optical glasses, polymethyl methacrylate, polycarbonate, polyallyl diglycol bis(allyl carbonate), polyvinyl fluoride, polyvinylidinefluoride, polytetrafluoroethylene, polycyclohexylene dimethylene terephthalate, polyethylene terephthalate, polymethylpentene, polyetherimide, polyurethane, nylon, acrylicimide, cellulose acetate butyrate, epoxy, and poly(styrene comethyl methacrylate)(2:1).

Suitable sealant layer materials include a polymer selected from the group consisting of polyvinyl alcohol, copolymers of polyvinyl alcohol with vinyl acetate, polyvinyl pyrrolidone, acrylics homopolymerized or copolymerized in emulsion, vinyl and styrenic homopolymers and copolymers prepared in emulsion, and vinyl homopolymers and copolymers.

Suitable barrier layer materials include polyvinyl alcohol, polyvinyl alcohol - co-vinyl acetate, polyvinyl pyrrolidone, methyl cellulose, polyethylene oxide, polypropylene oxide, and polyacrylic acid.

Colloidal particles are those in the range of about 1 to 500 nanometers, with the smaller sizes being best for silica particles in the shield of the present invention. The particle size should preferably be in the range of 1 to 100 nanometers, and the shields which have been made according to the invention used silica particles with sizes in the range of 30 to 50 nanometers.

Each silica particle represents a scattering center and the degree of scattering (measured by change in optical density) increases in approximate proportion to the number of particles in the optical path, viz.:

$$\Delta OD \approx \chi^{(3)} \times I \times l \times N_a/cm^3 \quad (1)$$

where:
$\chi^{(3)}$ is the third order nonlinear optical coefficient, also known as the third order susceptibility, of the silica particles[11];
I is the intensity of the incident light beam;
l is the length of the optical path through the silica particles; and
$N_a/cm^3$ is the number of particles of silica per cubic centimeter.

[11] When illuminated with Intensity I, if the third order susceptibility is a function of said intensity.

It has been found that the technique described above, involving the application of multiple sealant layers atop each active layer containing colloidal silica, enables a high particle density to be achieved while yielding a relatively high transmittance under ambient light conditions from moonless nights to bright sunny days.

The silica particles may be amorphous or crystalline. However, it is proven easier to obtain small particle sizes in amorphous silica. In the shields which were constructed, good results were obtained with fumed silica[12] which has an index of refraction of 1.46, can be made in the requisite extremely small particle sizes, forms small chain-like aggregates available in sizes in the 30 to 50 nanometer range, has a short-range-ordered glassy state,[13] nd a large surface area. Such fumed silica is available from Cab-O-Sil Division of Cabot Corporation, P.O. Box 188, Tuscola, Ill. 61953-0188.

[12] Made by hydrolysis of silicon tetrachloride vapor in a flame of hydrogen and oxygen.
[13] It is believed that this configuration results in enhanced third order nonlinear optical effects.

DETAILED DESCRIPTION

As seen in the illustrative embodiment of FIG. 1, a glass substrate 10 is symmetrically and sequentially covered on each its opposed major surfaces with a first active layer 11 (or 11'), three sealant layers 12, 13, 14 (or 12', 13', 14'), a barrier layer 15 (or 15'), an additional active layer 16 (or 16'), and three additional sealant layers 17, 18, 19 (or 17', 18', 19').[14]

[14] All descriptions which follow relating to any of layers 11 to 19 are equally applicable to layers 11' to 19' respectively.

The Active Layer

Active layer 11 consists of colloidal fumed silica particles with sizes in the 30 to 50 nanometer range dispersed in polyethylmethacrylate, a transparent organic binder which adheres well to colloidal silica. The fumed silica particles have been pretreated with hexamethyl disilazane to render it hydrophobic. This treatment permits the incorporation of higher concentrations of silica in the active layer.

Colloidal silica is commercially available from a number of sources as chain molecules of amorphous silica of varying width and length. Both the dry powder and dispersions in water and inorganic solvents such as methanol, ethylene glycol, dimethylacetamide and ethylene glycol mono-propyl ether are available. All grades and forms of colloidal silica can be used to fabricate the shield of the present invention.

The layer 11 has a thickness in the range of 10 to 50 microns, with a thickness of about 25 microns being preferred.

The active layer 11 is deposited by immersing the substrate 10 at room temperature in a toluene solution containing 10% by weight of polyethyl methacrylate and 6% by weight of colloidal fumed silica, the surface of which has been treated with hexamethyl disilazane to render it hydrophobic as previously mentioned. The immersion time is not critical, and is typically on the order of 5 to 10 seconds. Care is taken to minimize turbulence so as to prevent the formation of air bubbles which if incorporated in the active layer would decrease transmittance of ambient light.

After removal of the substrate from the toluene solution the active layer 11 is air dried at room temperature for about 10 minutes, and subsequently at 80° C. for about 10 minutes.

Binder Materials

In choosing a binder for the active layer, it is necessary to consider[15] that different transparent polymers possess different binding capabilities or affinity or compatibility for colloidal silica. Acrylics are particularly effective and versatile as binders for colloidal silica in the active layer. They comprise a broad array of homopolymers and copolymers in which the major monomeric constituents belong to esters of acrylic and methacrylic acids. These esters are used singly or in combination, sometimes with other monomers, to give polymeric products ranging from soft, flexible elastomers to hard, stiff thermoplastics and thermosets. Acrylics transmit 92% of white light, equaling the clarity of optical glass. Haze measurements of 1% to 3% are typical. Long term weathering of acrylics shows no significant change in color or physical properties.
[15] In addition to the index of refraction of the binder.

For these reasons acrylics are useful as binder material in the active layers as well as material for the sealant layers.

Examples of transparent polymers for use as binders in each active layer and for use as the sealant layers using an aqueous medium are polyvinyl alcohol and its copolymers with vinyl acetate, other water soluble transparent polymers such as polyvinyl pyrrolidone, and water emulsions of water insoluble polymers that are transparent. The latter includes acrylics homopolymerized or copolymerized in emulsion, and all vinyl and styrenic homopolymers and copolymers prepared in emulsion and that are transparent. Preferably, film forming emulsions or those that form a film at room temperature can be used. Solutions of optically transparent vinyl homopolymers and copolymers can be used in the various layers provided that they do not attack the substrate and thus degrade the transmittance thereof.

Examples of transparent polymers suitable as binders in the active layer and as candidates for the sealant layer include the following: polymethyl acrylate, polyethyl acrylate, polybutyl acrylate, poly 2-ethylhexyl acrylate, polymethyl methacrylate, polyethylmethacrylate, polybutylmethacrylate, various copolymers and mixtures of polymers of acrylates and methacrylates, polyvinyl acetate with different percentages of hydrolysis including polyvinyl alcohol, polystyrene, poly p-methyl styrene, poly α-methyl styrene, copolymers of vinyl chloride, copolymers of vinylidene chloride, copolymers of ethylene such as with vinyl acetate and vinyl chloride, cellulose acetate, cellulose triacetate, cellulose nitrate, cellulose acetate isobutyrate, silicone resins, polyvinylcarbazole, polyvinylbutyral and polyvinylformal.

The Sealant Layers

The active layer 11 is covered by a polyethylmethacrylate sealant layer 12 which is believed to contain silica particles which have diffused, leached or migrated from the active layer 11 into the sealant layer 12 during the process of its deposition from the liquid state.

After drying, the active layer 11 is coated with the sealant layer 12 by immersion in a toluene solution of 10% by weight of polyethyl methacrylate, and subsequently air dried at room temperature. The immersion time is not critical, and is typically on the order of 5 to 10 seconds. The drying tims is typically about 10 minutes.

The sealant layer 12 is then subjected to a brief heat treatment in an air circulating oven, for a time of 5 to 10 minutes at a temperature between 60° C. and 80° C., to completely remove the volatile toluene solvent.

Thereafter additional sealant layers such as 13 and 14 are deposited using the same technique as was used to deposit the sealant layer 12.

The thickness of each sealant layer is typically in the range of 10 to 50 microns.

While a total of three sealant layers atop each active layer is shown in FIG. 1 for illustrative simplicity, in practice nine to sixteen sealant layers are typically deposited atop each active layer. The higher the concentration of silica in the active layer, the greater the number of sealant layers which are needed for good transmittance of ambient light.

The application of the sealant layer 12 increases the visual transmittance through the substrate/active layer/sealant layer partially completed shield structure; typically from 10% transmittance prior to application of the sealant layer 12, to 30% transmittance after application of said sealant layer. Subsequent applications of sealant layers 13 and 14 increase the transmittance further. With a sufficient number of sealant layers the transmittance through the substrate 10, active layer 11 and sealant layers thereon increases to close to 90%.

However, at least four active layers are typically needed in order to provide the desired optical density changes of four or more between ambient light and exposure to a laser beam.

The Barrier Layer

In order to facilitate deposition of an additional active layer 16 above the outermost sealant layer 14, a barrier layer 15 is deposited on the outermost sealant layer after a sufficient number of sealant layers has been deposited to bring the transmittance through the substrate and the deposited layers to a high value, typically close to 90%.

The barrier layer 15 preferably comprises a substance which in the liquid state does not act as a solvent for the material of the sealant layer 14. A solution of 10% by weight of polyvinyl alcohol in water is preferred for use with the active and sealant layers described above.

To deposit the barrier layer 15, the outermost sealant layer is immersed in the polyvinyl alcohol solution and subsequently air dried at room temperature. The immersion time is not critical and is usually on the order of 5 to 10 seconds. The drying time is typically about 15 minutes. The thickness of the barrier layer is typically in the range of 10 to 50 microns.

The Additional Active Layer etc.

After the barrier layer 15 has dried, the coating process is then repeated to deposit an additional active layer 16. Additional sealant layers such as 17 to 19 are then deposited to increase the transmittance. If additional active layers are desired, additional barrier layer/active layer/sealant layer groupings are deposited.

As the number of active layers increases, the optical density change and thus the extent of protection against laser beams increases; while the overall transmittance decreases. With the arrangement illustrated in FIG. 1 and described above, optical density changes of four or more have been achieved with transmittances of better than 20%.

An objective in the coating process is to deposit many active layers of silica while achieving an acceptable transmittance in the final device.

In order to limit the number of cycles of active layer/-sealant layers/barrier layer deposition, several coats of the silica dispersion[16] used to form the active layer can be sequentially applied to the substrate, until the percent transmittance drops to a level of about 10%. After the last coat of silica dispersion is dried, several sealant layers are deposited, until the transmittance approaches 90%. The barrier coat is next applied and the active layer/sealant layers/-barrier layer deposition process is repeated.[17]

[17] For many applications this minimum acceptable level of overall transmittance is about 10%.

In general, the change in optical density $\Delta OD$ increases as the number of optical layers increases; and the percent visual or ambient transmittance increases with increasing numbers of sealant layers. In principle, a $\Delta OD$ of 4 with a percent visual transmittance of 80 to 90% is possible if the laminate is thick enough.

In the dipping or immersion process, there are certain limits which prevent the construction of a very thick laminate by repeated applications of the active layer dispersion and sealant layer and barrier layer solutions.

For example, after about five repeated coats of the active layer using 6% silica by weight in the dispersion, the silica in each layer begins to agglomerate and separate from the individual layer. Cracking of the film typically accompanies this separation. This agglomeration and cracking problem can be remedied by starting with a lower concentration of colloidal silica.

As previously described, the preferred technique to prevent this agglomeration and cracking problem is to deposit one active layer to provide shielding (while unavoidably decreasing transmittance), coat this active layer with multiple sealant layers to increase the transmittance, and repeat this process until the percent visual transmittance drops to a level which is the minimum considered acceptable for the particular use to which the shield is to be put.[17] Agglomeration eventually occurs here also, but this coating method permits an increase in the number of active layers that can be deposited using a specific concentration of colloidal silica in the binder.

The Preferred Embodiment

Experiments were conducted to determine the effect of the number of active layers on overall transmittance and change in optical density. In these experiments the general structure shown in FIG. 1 was employed, with each active layer being covered with a sufficient number of sealant layers to maximize the transmittance. The results of the experiments appear in Table 1, wherein (i) the left column shows the percent concentrations by weight of polymethacrylate binder and silica in the toluene solution used to deposit each active layer, (ii) the next column shows the number of active layers, each of which is separated from the other active layers by sealant or barrier layers, (iii) the next column shows overall percent transmittance through the entire multi-layer structure and substrate,[18] and (iv) the right column shows overall optical density change between ambient indoor lighting conditions and a YAG laser beam having a pulse width of 7 nanoseconds, a peak intensity of 5 mJ/cm$^2$, and an energy content of 5 mJ/pulse.[19] Changes in optical density were measured by determining the amount of energy going through the shield, as sensed by a Model 36-5002(365) digital power and energy indicator utilizing a Model 380101 disc calorimeter; both of which were purchased from Scientech, Inc. 5649 Arapahoe Avenue, Boulder, Colo. 80303.[20]

Figure 2:
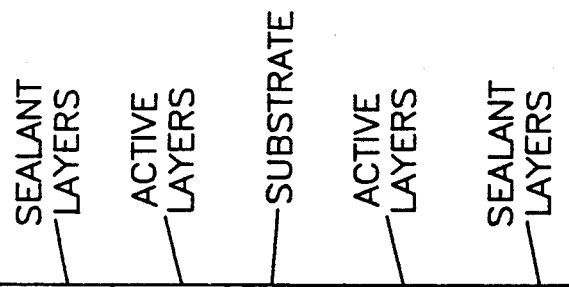
FIG. 2 shows in diagrammatic fashion the structure of an optical shield according to a first specific embodiment of the present invention.
Figure 3:
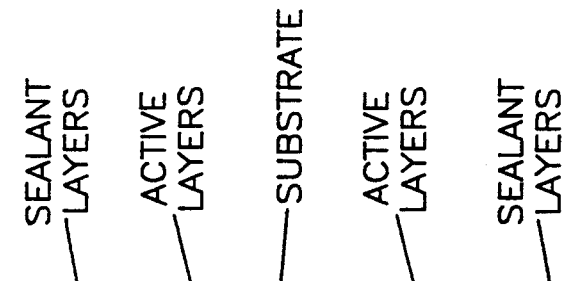
FIG. 3 shows in diagrammatic fashion the structure of an optical shield according to a second specific embodiment of the present invention.

[18] All transmittance measurements referred to herein were performed at a wavelength of 532 nanometers corresponding to the midpoint of the visible spectrum.
[19] All optical density data shown in FIGS. 2, 3 and 4 was also obtained on the basis of the change between these ambient and laser illumination conditions.
[20] For additional information on the use of calorimeters to measure laser output, see Measuring Laser Output, Lasers & Optronics, September 1991, p. 57–63. density, namely that an increase in one of these parameters is obtained only at the cost of a decrease in the other.

Table 1 shows that little is gained in terms of transmittance of optical density change by substantially increasing the number of active layers beyond two. It also reflects the inherent tradeoff between transmittance and change in optical density, namely that an increase in one of these parameters is obtained only at the cost of a decrease in the other.

TABLE 1

| Binder/Silica Ratio by weight | Number of Active Layers | Overall Percent Transmittance | Overall Change In Optical Density ($\Delta OD$) |
|---|---|---|---|
| 10/2 | 2 | 20 | 1.2 |
| 10/2 | 28 | 20 | 1.4 |
| 10/3 | 2 | 11 | 1.5 |
| 10/3 | 28 | 10 | 3.0 |
| 10/4 | 2 | 9 | 3.0 |
| 10/4 | 10 | 9 | 3.0 |
| 10/5 | 2 | 12 | 1.8 |
| 10/5 | 8 | 16 | 1.6 |
| 10/6 | 2 | 28 | 1.1 |
| 10/6 | 4 | 24 | 1.1 |

First Embodiment - FIG. 2

FIG. 2 is a diagram showing an optical shield according to a first embodiment of the present invention, and includes four columns containing data concerning this embodiment.

As shown in FIG. 2, on each side of the glass substrate two active layers 21, 22 are deposited directly atop each other, from a toluene solution containing 10% by weight of polyethylmethacrylate and 4% by weight of colloidal silica dispersed therein. Nine sealant layers 23, 24 are sequentially deposited on each of the active layer groups 21, 22 respectively.

The glass substrate 20 exhibits a transmittance of 92% and no optical density change. After the active layers 21, 22 are deposited, the overall transmittance through these layers and the substrate is 11% and the overall optical density change is 1.7. After the sealant layers 23, 24 are deposited, the overall transmittance has increased to 90% while the overall optical density change has dropped to 0.8.

Second Embodiment - FIG. 3

FIG. 3 is a diagram showing an optical shield according to a second embodiment of the present invention, and includes data columns similar to those of FIG. 2.

As shown in FIG. 3, on each side of the glass substrate four active layers 26, 27 are deposited directly atop each other, from a toluene solution containing 10% by weight of polyethylmethacrylate and 5% by weight of colloidal silica dispersed therein. Nine sealant layers 28, 29 are sequentially deposited on each of the active layer groups 26, 27 respectively.

The glass substrate 25 exhibits a transmittance of 92% and no optical density change. After the active layers 26, 27 are deposited, the overall transmittance through these layers and the substrate is 16% and the overall optical density change is 1.6. After the sealant layers 28, 29 are deposited, the overall transmittance has increased to 78% while the overall optical density change has dropped to 1.2.

Preferred Embodiment - FIG. 4

FIG. 4 is a diagram showing an optical shield according to a preferred embodiment of the present invention, and includes data columns similar to those of FIGS. 2 and 3.

As shown in FIG. 4, on each side of the glass substrate four active layers 31, 32 are deposited directly atop each other, from a toluene solution containing 10% by weight of polyethylmethacrylate and 6% by weight of colloidal silica dispersed therein. Sixteen sealant layers 33, 34 are sequentially deposited on each of the active layer groups 31, 32 respectively. Barrier layers 35, 36 are deposited on the outermost of each of the sealant layer groups 33, 34.

Four additional active layers 37, 38 are deposited directly atop each other, from a toluene solution containing 10% by weight of polyethylmethacrylate and 6% by weight of colloidal silica dispersed therein. Sixteen additional sealant layers 39, 40 are sequentially deposited on each of the additional active layer groups 37, 38 respectively.

The glass substrate 30 exhibits a transmittance of 92% and no optical density change. After the active layers 31, 32 are deposited, the overall transmittance through these layers and the substrate is 24% and the overall optical density change is 1.0. After the sealant layers 33, 34 are deposited, the overall transmittance has increased to 85% while the overall optical density change has dropped to 0.9. After the barrier layers 35, 36 are deposited, the overall transmittance has dropped slightly to 81% and there is no change in the change in optical density. After the additional active layers 37, 38 are deposited, the overall transmittance through all layers and the substrate is 18% and the overall optical density change is 1.1. After the additional sealant layers 39, 40 are deposited, the overall transmittance has increased to 79% while the overall optical density change has increased to 1.2.

When the shield of FIG. 4 was subjected to a Nd;YAG[21] laser beam with a pulse width of 2.5–7 nanoseconds at intensity levels of 1 microjoule per square centimeter or greater, the laser beam was virtually completely blocked, in that the amount of beam energy penetrating the shield was undetectable.[22] When subjected to increasing levels of laser beam energy, the shield demonstrated a saturation characteristic, in that at intensity levels above about 1 millijoule per square centimeter the amount of energy penetrating the shield increased at a greater rate with increase in incident laser beam intensity. This saturation characteristic indicates that the apparent third order susceptibility of the shield decreases at such elevated intensity levels.

[21] Neodymium; Yttrium-aluminum-garnet
[22] The detection apparatus had a sensitivity of $10^{-4}$ microjoules per square centimeter.

Other Embodiments

In manufacturing optical shields according to the present invention, the most time consuming operation is the application of multiple sealant coats to increase the visual transmittance of the shield.

The number of sealant coats required can be reduced if a solution containing a higher concentration of polymer[23] is used. A solution containing up to 50 weight percent polymer can be used, depending on the molecular weight of the polymer. In principle, 100% solids systems such as UV-curable, two part catalyzed, and hot melts arrangements can be used to prepare thicker films.

[23] Polyethylmethacrylate in the preferred embodiment.

The solution method of coating appears to give the best results at the present time, but it is likely that mechanical application of the various coatings would improve the optical quality of the films.

For example, various films may be laminated together to form the multilayered device comprising multiple groups of substrate/-active layer/sealant layers/barrier layer, where the number of groups is limited by the desired level of visual transmittance of the shield.

An optically transparent adhesive can be used to laminate each film to the next. The rest or ambient optical density of the laminate is equal to the sum of the optical densities of each film in the laminate. The change in optical density $\Delta OD$ is also additive if the laminate is properly configured.

Solventless systems (100% solids systems) can also be used to deposit the various layers of the optical shield of the present invention. These include catalyzed two-part systems such as transparent epoxies and polyesters, UV-curable systems, including high boiling acrylic and methacrylic esters and urethane acrylates and methacrylates, which have low viscosities and do not contain organic solvents, and hot melt adhesives capable of yielding transparent films.

Examples of clear substrates suitable for use in making a shield according to the present invention are inorganic oxide optical glasses, transparent and inert plastics such as polymethyl methacrylate, polycarbonate, polyallyl diglycol bis(allyl carbonate), polyvinyl fluoride, polyvinylidine fluoride, polytetrafluoroethylene, polycyclohexylene dimethylene terephthalate, polyethylene terephthalate, polymethylpentene, polyetherimide, polyurethane, nylon, acrylic-imide, cellulose acetate butyrate, epoxy, and poly(styrene co-methyl methacrylate)(2:1), and other transparent polymers capable of being processed into thin films suitable for lamination. The surfaces of these films can be treated to permit adhesion of both the optical layer and the barrier layer. The only restriction for the clear substrate is that the solvent should not attack (dissolve or etch) it because this degrades the visual performance of the device.

Free standing thin films of silica dispersed in the organic polymer would be desirable because they can be easily laminated to clear films to produce a laminate. However, this is impractical because of the difficulty in preparing such films with 20–40% silica having adequate mechanical integrity.

A mechanical support or substrate is necessary for films containing high concentrations of silica in the active layer. Thus a coating process is required for depositing many coatings on the same substrate because, as previously discussed, solution coating contributes to higher visual transmittance.

It is to be understood that the embodiments described above are merely illustrative of some of the many specific embodiments which represent applications of the principles of the present invention. Clearly, numerous other arrangements may be readily devised by those skilled in the art without departing from the spirit and scope of the invention.

I claim:

1. A nonlinear optical shield, comprising:

a transparent substrate having opposed major surfaces;
an active layer disposed on one of said major surfaces, said layer comprising colloidal silica particles dispersed in a transparent binder;
a transparent sealant layer disposed on a surface of said active layer remote from said substrate;
a transparent barrier layer disposed on said sealant layer; and
an additional active layer comprising colloidal silica particles dispersed in a transparent binder disposed on said barrier layer.

2. A nonlinear optical shield, comprising:
a transparent substrate having opposed major surfaces;
an active layer disposed on one of said major surfaces, said layer comprising silica particles having sizes in the range of 1 to 100 nanometers dispersed in a transparent binder which is not significantly photorefractive relative to said particles and which has an index of refraction on the same order as that of said particles; and
a transparent sealant layer disposed on a surface of said active layer remote from said substrate.

3. A nonlinear optical shield, comprising:
a transparent substrate having opposed major surfaces; and
a stack of nonlinear optical sections disposed on at least one major surface of said substrate, said stack comprising:
a plurality of active layers of colloidal silica particles dispersed in a transparent binder, and
transparent isolation means separating each active layer from adjacent active layers.

4. The shield according to claim 1 or 3, wherein said particles and said binder have indices of refraction on the same order.

5. The shield according to claim 3, wherein said isolation means has an index of refraction substantially different from the index of refraction of said binder so that substantial refraction of incident light occurs at each interface between an active layer and adjacent isolation means.

6. The shield according to claim 1 or 3, wherein said binder comprises a material which is not substantially photorefractive.

7. The shield according to claim 1, wherein said binder is an organic polymer.

8. The shield according to claim 1 or 3, wherein said binder comprises an acrylic plastic.

9. The shield according to claim 1 or 3, wherein said binder is selected from the group consisting of polyethyl methacrylate, polyethyl acrylate, polybutyl acrylate, poly 2-ethylhexyl acrylate, polymethyl methacrylate, polyethylmethacrylate, polybutylmethacrylate, various copolymers and mixtures of polymers of acrylates and methacrylates, polyvinyl acetate with different percentages of hydrolysis including polyvinyl alcohol, polystyrene, poly p-methyl styrene, poly α-methyl styrene, copolymers of vinyl chloride, copolymers of vinylidene chloride, copolymers of ethylene such as with vinyl acetate and vinyl chloride, cellulose acetate, cellulose triacetate, cellulose nitrate, cellulose acetate isobutyrate, silicone resins, polyvinylcarbazole, polyvinylbutyral and polyvinylformal.

10. The shield according to claim 1 or 3, wherein said binder has an index of refraction in the range of 1.4 to 1.5.

11. The shield according to claim 1 or 3, wherein said silica is amorphous.

12. The shield according to claim 1 or 3, wherein said silica is in a short-range-ordered glassy state.

13. The shield according to claim 1 or 3, wherein said particles have a size in the range of 1 to 100 nanometers.

14. The shield according to claim 1 or 3, wherein said particles have a size in the range of 30 to 50 nanometers.

15. The shield according to claim 1 or 3, wherein said substrate is a polymer.

16. The shield according to claim 1 or 3, wherein said substrate is selected from the group consisting or inorganic oxide optical glasses, polymethyl methacrylate, polycarbonate, polyallyl diglycol bis(allyl carbonate), polyvinyl fluoride, polyvinylidine fluoride, polytetrafluoroethylene, polycyclohexylene dimethylene terephthalate, polyethylene terephthalate, polymethylpentene, polyetherimide, polyurethane, nylon, acrylicimide, cellulose acetate butyrate, epoxy, and poly(styrene co-methyl methacrylate)(2:1).

17. The shield according to claim 1, wherein said sealant layer comprises the same material as said binder.

18. The shield according to claim 1, wherein said sealant layer comprises a substance in which said binder is soluble.

19. The shield according to claim 1, wherein said sealant layer comprises a polymer selected from the group consisting of polyvinyl alcohol, copolymers of polyvinyl alcohol with vinyl acetate, polyvinyl pyrrolidone, acrylics homopolymerized or copolymerized in emulsion, vinyl and styrenic homopolymers and copolymers prepared in emulsion, and vinyl homopolymers and copolymers.

20. The shield according to claim 3, wherein said isolation means comprises polyvinyl alcohol.

21. The shield according to claim 1 or 3, wherein the thickness of each active layer is in the range of 10 to 50 microns.

22. The shield according to claim 3, wherein said isolation means comprises a barrier layer of a material in which any adjacent binder is not soluble.

23. The shield according to claim 1, wherein said active layer comprises 5% to 40% silica by weight.

24. The shield according to claim 3, wherein each active layer comprises 5% to 40% silica by weight.

25. The shield according to claim 1 or 3, wherein additional ones of said layers are disposed on the other major surface of said substrate in the same order as on said one major surface thereof, so that said substrate is centrally disposed between and symmetrically surrounded by said layers.

* * * * *